United States Patent [19]

Duemmen

[11] Patent Number: Plant 7,059

[45] Date of Patent: Nov. 28, 1989

[54] DUEROM

[76] Inventor: Guenter Duemmen, Dammweg 18-20, D-4134 Rheinberg 4, Fed. Rep. of Germany

[21] Appl. No.: 196,279

[22] Filed: May 20, 1988

[51] Int. Cl.[4] ..... A01H 5/00

[52] U.S. Cl. ..... Plt./68

[58] Field of Search ..... Plt. 68

*Primary Examiner*—Robert E. Bagwill

*Attorney, Agent, or Firm*—Marks Murase & White

[57] ABSTRACT

A new and distinct geranium plant known by the cultivar name Duerom is characterized by a new color, dark foliage with zonation, very good durability under outdoor summer conditions, and a great number of large umbels with many flowers.

1 Drawing Sheet

The present invention comprises a new distinct cultivar of geranium, botanically known as *Pelargonium zonale,* and hereinafter referred to by the cultivar name Duerom.

Duerom is a product of planned breeding program which had the objective of creating new geranium cultivars with a new kind of color, robust foliage and umbel.

Duerom was originated from a hybridization made in a controlled breeding program in Rheinberg, Federal Republic of Germany in 1983/84. The female parent was an unnamed seedling. The male parent of Duerom was an unnamed seedling.

Duerom was discovered and selected as one flowering plant within the progeny of the stated cross by Guenter Duemmen in 1985 in a controlled environment in Rheinberg.

The first act of asexual reproduction of Duerom was accomplished when vegetative cuttings were taken from the initial selection in July, 1985 in a controlled environment in Rheinberg by a technician working under formulations established and supervised by Guenter Duemmen. Horticultural examination of selected units initiated in October, 1985 has demonstrated that the combination of characteristics as herein disclosed for Duerom are firmly fixed and are retained through successive generations of asexual reproduction.

Duerom has not been observed under all possible environmental conditions. The phenotype may vary significantly with variations in environment such as temperature, light intensity, and day length. The following observations, measurements, and comparisons describe plants grown in Rheinberg under greenhouse conditions which approximate those generally used in commercial practice.

The following traits have been repeatedly observed and are determined to be basic characteristics of Duerom which in combination distinguish this geranium as a new and distinct cultivar:

1. New kind of color;
2. Dark foliage with zonation;
3. Very good durability under outdoor summer conditions;
4. Great number of big umbels with many flowers.

Of the many commercial cultivars known to the present inventor none are believed to be similar in comparison to Duerom.

The accompanying photographic drawings show typical flower and foliage characteristics of Duerom with colors being as true as possible with illustrations of this type.

In the following description color references are made to The Royal Horticultural Society Color Chart. The color values were determined between 10.00–14.00 on Oct. 12, 1988 under natural light conditions at Rheinberg.

Classification:

*Botanical.*—*Pelargonium zonale* cv. Duerom.

*Commercial.*—Geranium.

INFLORESCENCE

A. Umbel:
- *Average diameter.*—9.5–11 cm.
- *Average depth.*—5.5–6.5 cm.
- *Peduncle length.*—16.5–18 cm.
- *Pedicel length.*—2.5–3.5 cm.

B. Corolla:
- *Average diameter.*—4 cm.
- *Form.*—semi-double.
- *Color (general tonality from a distance of three meters).*—RHS 68D.
- *Color (abaxial).*—RHS 68A.
- *Color (adaxial).*—RHS 69B.

C. Bud:
- *Shape.*—Elliptic.
- *Color* (abaxial).—RHS 69A.
- *Color* (adaxial).—RHS 62D.

D. Reproductive organs:
- *Androecium.*—Fertil, obdiplostemon, centrifugal dedouplement.
- *Gynoecium.*—5-lobed stigma. pubescent, 5 carpels, coenocarp, hypogyn.

E. Spring flowering response period:
- *FRG.*—50% of plants with at least one flower open 13 weeks after stick of unrooted cuttings.

F. Outdoor flower production: Very good.

G. Durability: Very good.

PLANT

A. Foliage:
- *Form.*—round.
- *Margin.*—bicrenated, Type 1.
- *Color (abaxial).*—RHS 137C.
- *Color (adaxial).*—RHS 138B.
- *Color (zonation).*—RHS 137B.
- *Tolerance of botyrtis.*—good.

B. General appearance and form:

*Internode length.*—Medium.
*Branching pattern.*—Good.
*Height.*—medium — high.

What is claimed is:

1. A new and distinct cultivar of geranium known as

Duerom, as described and illustrated, and particularly characterized by a new color, dark foliage with zonation, very good durability under outdoor summer conditions, and a great number of large umbels with many flowers.

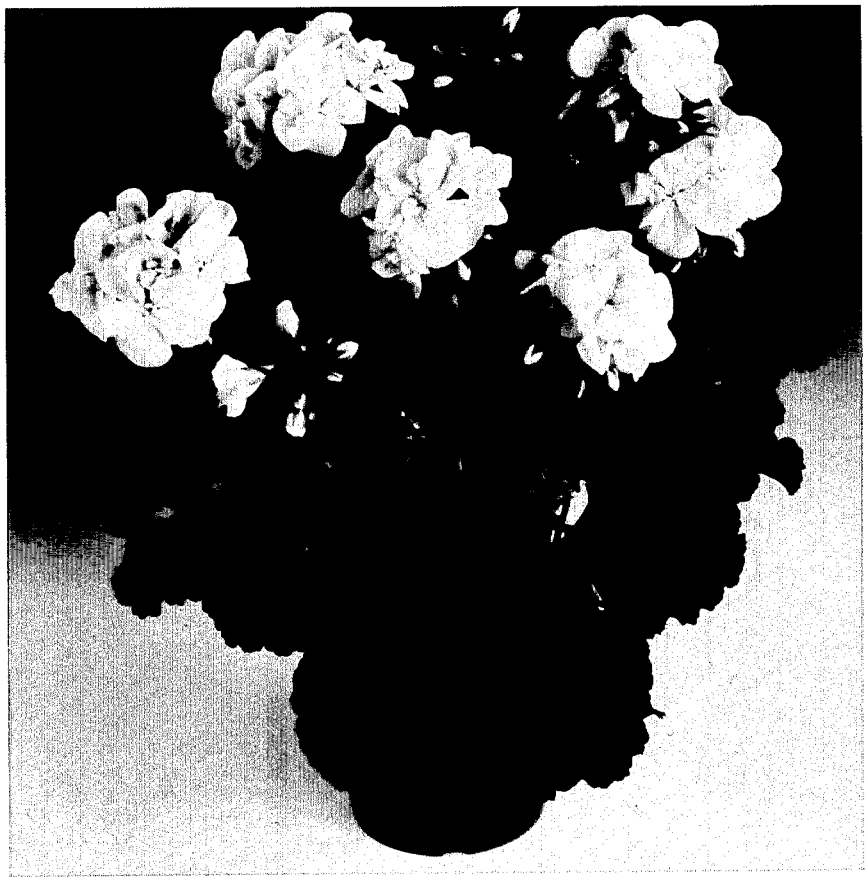

* * * * *